US011733505B2

(12) United States Patent
Katakura

(10) Patent No.: US 11,733,505 B2
(45) Date of Patent: Aug. 22, 2023

(54) ENDOSCOPE

(71) Applicant: OLYMPUS CORPORATION, Hachioji (JP)

(72) Inventor: Masahiro Katakura, Chofu (JP)

(73) Assignee: OLYMPUS CORPORATION, Tokyo (JP)

( * ) Notice: Subject to any disclaimer, the term of this patent is extended or adjusted under 35 U.S.C. 154(b) by 297 days.

(21) Appl. No.: 17/239,850

(22) Filed: Apr. 26, 2021

(65) Prior Publication Data

US 2021/0239964 A1    Aug. 5, 2021

Related U.S. Application Data

(63) Continuation of application No. PCT/JP2018/040112, filed on Oct. 29, 2018.

(51) Int. Cl.
*G02B 23/24* (2006.01)
*G02B 15/14* (2006.01)
(Continued)

(52) U.S. Cl.
CPC ............ *G02B 23/2469* (2013.01); *A61B 1/04* (2013.01); *G02B 15/143507* (2019.08);
(Continued)

(58) Field of Classification Search
CPC ........ G02B 23/2469; G02B 15/143507; G02B 23/2438; G02B 23/2461; G02B 27/0075;
(Continued)

(56) References Cited

U.S. PATENT DOCUMENTS

| 5,774,214 A | 6/1998 | Prettyjohns |
| 9,030,543 B2 | 5/2015 | Tsuyuki et al. |

(Continued)

FOREIGN PATENT DOCUMENTS

| JP | 2004313523 A | 11/2004 |
| JP | 5075658 B2 | 11/2012 |

(Continued)

OTHER PUBLICATIONS

International Preliminary Report on Patentability (IPRP) (and English language translation thereof) dated May 14, 2021 issued in International Application No. PCT/JP2018/040112.
(Continued)

*Primary Examiner* — Arnel C Lavarias
(74) *Attorney, Agent, or Firm* — Holtz, Holtz & Volek PC

(57) ABSTRACT

An endoscope includes a plurality of illuminating optical systems, an objective optical system, and an optical-path splitting member. The optical-path splitting member has an optical element which forms a first optical path and a second optical path, and an optical-path length of the first optical path differs from an optical-path length of the second optical path. Illumination light is irradiated to an object from the plurality of illuminating optical systems. The objective optical system has an object-side incidence surface which is located nearest to the object, and each of the plurality of illuminating optical systems has an object-side emergence surface which is located nearest to the object. Each of the object-side emergence surfaces is located on an image side of the object-side incidence surface, and following conditional expression (1) is satisfied:

$$2.0 < Dmin/OPLdiff < 50 \qquad (1).$$

6 Claims, 10 Drawing Sheets

(51) Int. Cl.
*G02B 27/00* (2006.01)
*G02B 27/10* (2006.01)
*A61B 1/04* (2006.01)

(52) U.S. Cl.
CPC ..... *G02B 23/2438* (2013.01); *G02B 23/2461* (2013.01); *G02B 27/0075* (2013.01); *G02B 27/1066* (2013.01)

(58) Field of Classification Search
CPC ............... G02B 27/1066; G02B 23/2407; G02B 23/24; G02B 21/00; G02B 21/0004; G02B 21/0028; G02B 21/0032; A61B 1/04; A61B 1/00064; A61B 1/00096; A61B 1/00117; A61B 1/00163; A61B 1/00165; A61B 1/00174; A61B 1/00181; A61B 1/00183; A61B 1/00188; A61B 1/002; A61B 1/042; A61B 1/05; A61B 1/051; A61B 1/06; A61B 1/0607; A61B 1/0627; A61B 1/0625; A61B 1/32
USPC ....... 359/432, 362, 363, 368, 369, 379, 380, 359/385, 387; 600/101, 109, 153, 160, 600/167, 168, 173, 176, 177, 178, 182
See application file for complete search history.

(56) References Cited

U.S. PATENT DOCUMENTS

| | | |
|---|---|---|
| 9,757,012 B2 | 9/2017 | Katakura |
| 9,851,551 B2 | 12/2017 | Katakura |
| 2013/0041215 A1* | 2/2013 | McDowall ........... G02B 27/283 600/109 |
| 2014/0176692 A1 | 6/2014 | Tsuyuki et al. |
| 2017/0052359 A1 | 2/2017 | Katakura |

FOREIGN PATENT DOCUMENTS

| | | | |
|---|---|---|---|
| JP | 5593004 B2 | 9/2014 | |
| JP | 5989290 B1 | 8/2016 | |
| WO | WO-2017199531 A1 * | 11/2017 | ............... A61B 1/00 |

OTHER PUBLICATIONS

International Search Report (ISR) (and English translation thereof) dated Dec. 25, 2018, issued in International Application No. PCT/JP2018/040112.
Written Opinion dated Dec. 25, 2018, issued in International Application No. PCT/JP2018/040112.

* cited by examiner

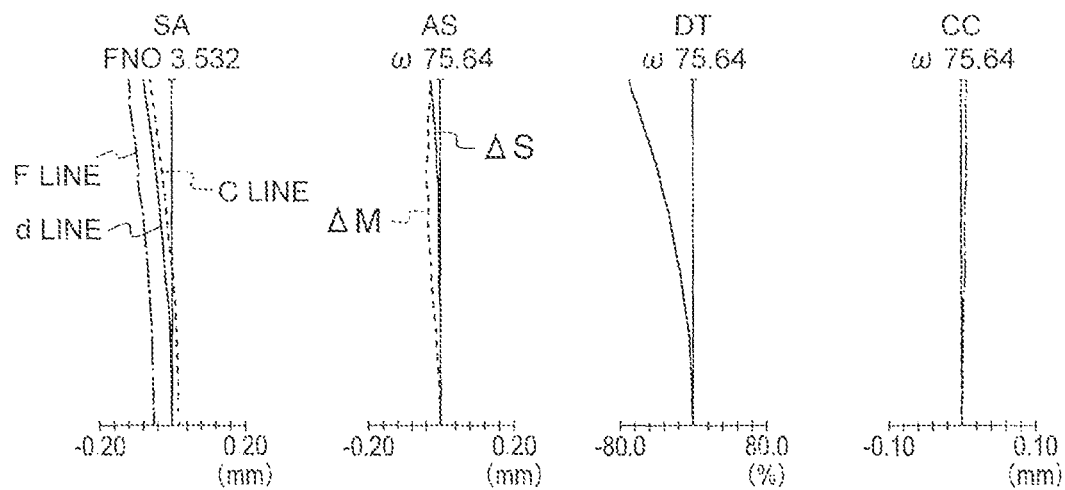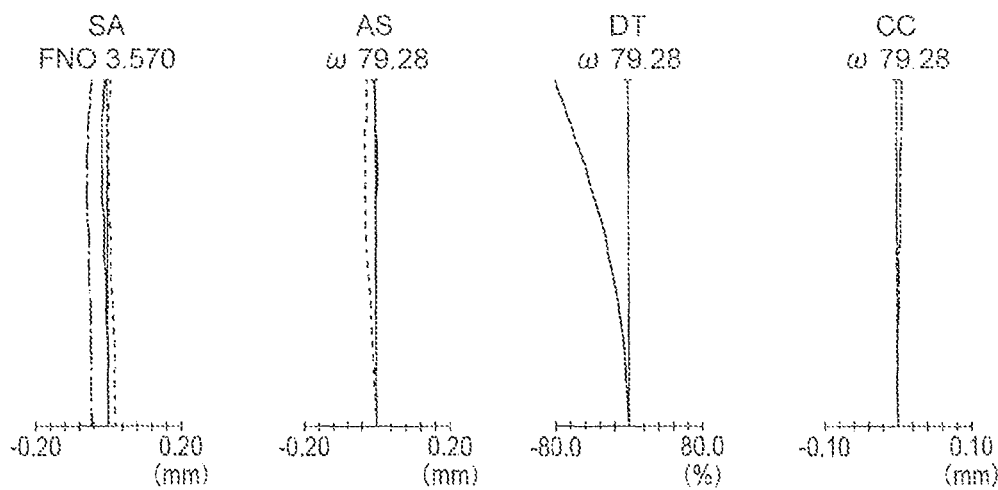

ENDOSCOPE

CROSS-REFERENCE TO RELATED APPLICATION

The present application is a continuation application of International Application No. PCT/JP2018/040112 filed on Oct. 29, 2018, the entire contents of which are incorporated herein by reference.

BACKGROUND

Technical Field

The present disclosure relates to an endoscope.

Description of the Related Art

An endoscope which includes a plurality of illuminating optical systems has been known. By using the plurality of illuminating optical systems, it is possible to illuminate a field of view with a uniform brightness.

In Japanese Patent No. 5075658 Publication, an endoscope which includes a first illuminating optical system and a second illuminating optical system has been disclosed. An angle of irradiation light and an amount of emergence light differ for the first illuminating optical system and the second illuminating optical system. In the illuminating optical systems of this endoscope, it is possible to adjust an angle of illumination and to restrict an amount of light. Therefore, this endoscope is superior from a point of reducing an illumination unevenness.

In Japanese Patent No. 5989290 Publication, an endoscope which includes three illuminating optical systems has been disclosed. In the three illuminating optical systems, each lens surface at a front-end portion is located at a base-end side of a lens surface of a front end of an observation optical system. The illuminating optical systems being disposed three-dimensionally, it is easy to reduce the illumination unevenness.

In Japanese Patent No. 5593004 Publication, an endoscope system which includes an objective optical system and an optical-path splitter has been disclosed. Two optical images with different focus are formed by the optical-path splitter. It is possible to acquire an image of a deep depth of field from the two optical images.

SUMMARY

An endoscope according to at least some embodiments of the present disclosure includes:
a plurality of illuminating optical systems,
an objective optical system, and
an optical-path splitting member, wherein
the optical-path splitting member has an optical element which forms a first optical path and a second optical path,
an optical-path length of the first optical path differs from an optical-path length of the second optical path,
illumination light is irradiated to an object from the plurality of illuminating optical systems,
the objective optical system has an object-side incidence surface which is located nearest to the object,
each of the plurality of illuminating optical systems has an object-side emergence surface which is located nearest to the object,
each of the object-side emergence surfaces is located on an image side of the object-side incidence surface, and following conditional expression (1) is satisfied:

$$2.0 < D\text{min}/\text{OPLdiff} < 50 \tag{1}$$

where,
Dmin denotes a minimum of depth amounts, and the depth amount is a distance in an optical axial direction from the object-side incidence surface up to the object-side emergence surface, and
OPLdiff denotes a difference in the optical-path length of the first optical path and the optical-path length of the second optical path.

BRIEF DESCRIPTION OF THE DRAWINGS

FIG. 6A, FIG. 6B, FIG. 6C, FIG. 6D, FIG. 6E, FIG. 6F, FIG. 6G, and FIG. 6H are aberration diagrams of the objective optical system of the example 1;

DETAILED DESCRIPTION

An embodiment and examples of an endoscope according to the present disclosure will be described below in detail by referring to the accompanying diagrams. However, the present disclosure is not restricted to the embodiment and the examples described below.

An endoscope of the present embodiment includes a plurality of illuminating optical systems, an objective optical system, and an optical-path splitting member. The optical-path splitting member has an optical element which forms a first optical path and a second optical path, and an optical-path length of the first optical path differs from an optical-path length of the second optical path. Illumination light is irradiated to an object from the plurality of illuminating optical systems. The objective optical system has an object-side incidence surface which is located nearest to the object, and each of the plurality of illuminating optical systems has an object-side emergence surface which is located nearest to the object. Each of the object-side emergence surfaces is located on an image side of the object-side incidence surface, and following conditional expression (1) is satisfied:

$$2.0 < D\text{min}/\text{OPLdiff} < 50 \tag{1}$$

where,
Dmin denotes a minimum of depth amounts, and the depth amount is a distance in an optical axial direction from the object-side incidence surface up to the object-side emergence surface, and OPLdiff denotes a difference in the optical-path length of the first optical path and the optical-path length of the second optical path.

Figure 1:
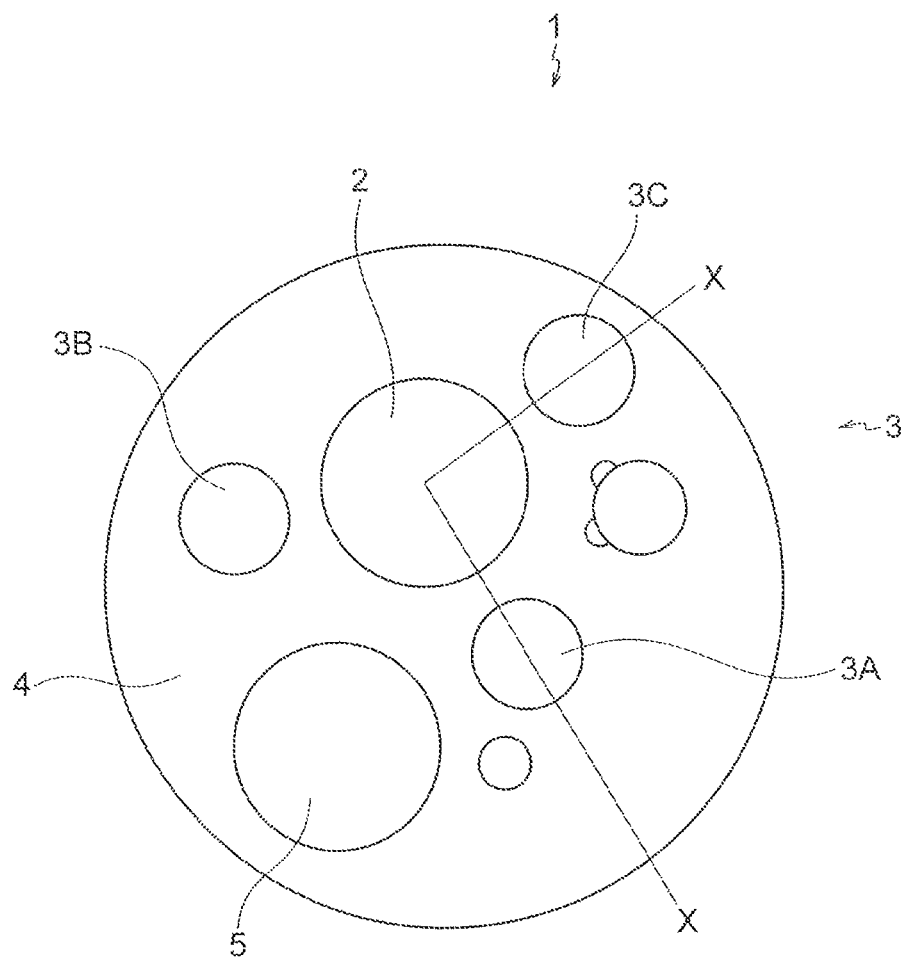
FIG. 1 is a diagram showing an endoscope of the present embodiment.
Figure 2:
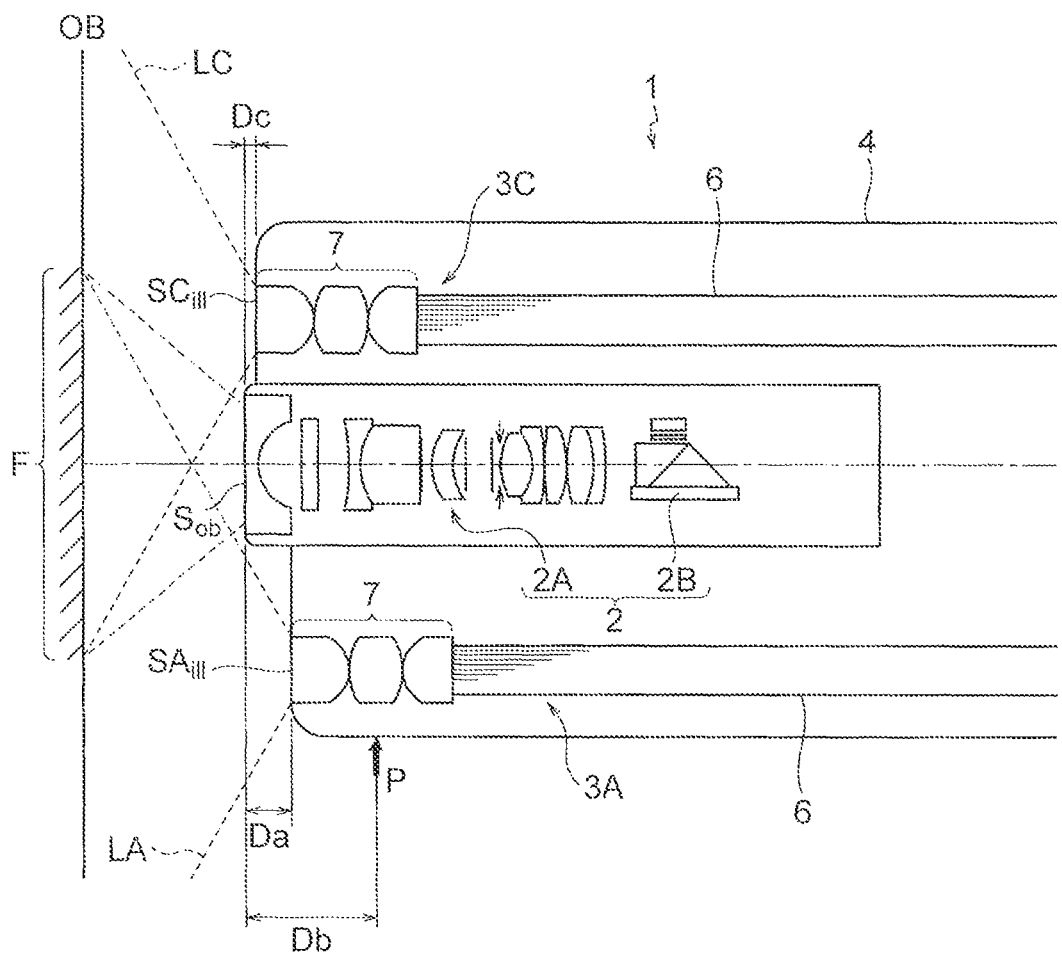
FIG. 2 is a diagram showing the endoscope of the present embodiment.

The endoscope of the present embodiment is shown in FIG. 1 and FIG. 2. FIG. 1 is a front view of a front-end portion of the endoscope. FIG. 2 is a cross-sectional view of the front-end portion of the endoscope. The cross-sectional view is a cross-sectional view about a line X-X shown in FIG. 1.

An endoscope 1 includes an objective optical system 2A, an optical-path splitting member 2B, and a plurality of illuminating optical systems 3. An objective unit 2 is formed by the objective optical system 2A and the optical-path splitting member 2B. The objective unit 2 and the plurality of illuminating optical systems 3 are disposed at a front-end portion 4 of an insertion portion. A forceps opening 5 is formed in the front-end portion 4.

The objective optical system 2A, for example, includes in order from an object side, a first lens group having a negative refractive power, a second lens group having a positive refractive power, an aperture stop, and a third lens group having a positive refractive power.

An optical filter is disposed in the first lens group. However, a location where the optical filter is to be disposed is not restricted to the first lens group. Moreover, the optical filter may not have been disposed.

The optical-path splitting member 2B is disposed on an image side of the objective optical system 2A. The optical-path splitting member 2B includes an optical element. The optical element has an optical surface. At the optical surface, incident light is divided into a reflected light and a transmitted light. As a result, for instance, the first optical path is formed in a direction of travel of the reflected light and the second optical path is formed in a direction of travel of the transmitted light. In such manner, a first optical path and a second optical path are formed by the optical-path splitting member 2B.

A first optical image is formed in the first optical path. A second optical image is formed in the second optical path. The first optical image and the second optical image are formed on the same plane. However, in the objective unit 2, an optical-path length of the first optical path differs from an optical-path length of the second optical path. Consequently, an object position conjugate with the plane on which the two optical images are formed differ in the first optical path and the second optical path. In such manner, in the objective unit 2, two optical images with different object positions are formed.

By capturing the first optical image and the second optical image, it is possible to achieve a first image and a second image. Each of the first image and the second image includes an area which is focused and an area which is not focused. And so, an image is combined by using only focused areas. By making such arrangement, it is possible to acquire an image in which a depth of field is widened.

The plurality of illuminating optical systems 3 includes an illuminating optical system 3A, an illuminating optical system 3B, and an illuminating optical system 3C. The illuminating optical system 3A, the illuminating optical system 3B, and the illuminating optical system 3C are provided around the objective unit 2.

Each of the illuminating optical system 3A and the illuminating optical system 3C includes an optical fiber bundle 6 and a lens group 7. Although it is not shown in the diagram, also the illuminating optical system 3B includes the optical fiber bundle 6 and the lens group 7.

The optical fiber bundle 6 guides illumination light L from a light source (not shown in the diagram) up to the lens group 7. The lens group 7 is disposed at an emergence end of the optical fiber bundle 6. Due to the lens group 7, the illumination light emerges as divergent light from the front-end portion 4. The illumination light is irradiated to an object OB.

The number of illuminating optical systems is not restricted to three. The number of illuminating optical systems may be two or not less than four.

The objective optical system 2A has an object-side incidence surface $S_{ob}$. The object-side incidence surface $S_{ob}$ is disposed nearest to the object in the objective optical system 2A.

The illuminating optical system 3A has an object-side emergence surface $SA_{ill}$. The object-side emergence surface $SA_{ill}$ is located nearest to the object in the illuminating optical system 3A. The illuminating optical system 3B has an object-side emergence surface $SB_{ill}$. The object-side emergence surface $SB_{ill}$ is located nearest to the object in the illuminating optical system 3B. The illuminating optical system 3C has an object-side emergence surface $SC_{ill}$. The object-side emergence surface $SC_{ill}$ is located nearest to the object in the illuminating optical system 3C.

An optical axis of the illuminating optical system 3A, an optical axis of the illuminating optical system 3B, and an optical axis of the illuminating optical system 3C are substantially parallel to an optical axis of the objective optical system 2A. The object-side incidence surface $S_{ob}$, the object-side emergence surface $SA_{ill}$, the object-side emergence surface $SB_{ill}$, and the object-side emergence surface $SC_{ill}$ are flat surfaces, and normals of the surfaces are substantially parallel. Accordingly, a direction of emergence of the illumination light L and a direction of observation in the objective optical system 2A are substantially parallel.

Illumination light LA emerges from the illuminating optical system 3A. Illumination light LC emerges from the illuminating optical system 3C. A field of view F of the observation optical system 3 is illuminated by a part of the illumination light LA and a part of the illumination light LC. Although it is not shown in the diagram, an illumination light emerges from the illuminating optical system 3B as well. Also a part of the illumination light emerged from the illuminating optical system 3B illuminates the field of view F.

The field of view F is illuminated from three directions. An illuminance distribution in the field of view F is achieved by adding the illumination light LA from the illuminating optical system LA, illumination light from the illuminating optical system 3B, and the illumination light LC from the illuminating optical system 3C.

As shown in FIG. 2, in the endoscope 1, the object-side emergence surface $SA_{ill}$ and the object-side emergence surface $SC_{ill}$ are located on the image side of the object-side incidence surface $S_{ob}$. Moreover, in FIG. 2, although the illuminating optical system 3B is not shown, a location indicated by an arrow P is a location of the object-side emergence surface $SB_{ill}$. Accordingly, the object-side emergence surface $SB_{ill}$ is also located on the image side of the object-side incidence surface $S_{ob}$.

The object-side emergence surface $SA_{ill}$ is located on the image side of the object-side emergence surface $SC_{ill}$. Moreover, the object-side emergence surface $SB_{ill}$ is located on the image side of the object-side emergence surface $SA_{ill}$. In such manner, a distance from the object-side incidence surface up to the object-side emergence surface (hereinafter, referred to as 'depth amount') differs for each illuminating optical system. In the endoscope 1, a relationship of the depth amounts is as follows.

$$Db < Da < Dc$$

where,

Da denotes a distance from the object-side incidence surface $S_{ob}$ up to the object-side emergence surface $SA_{ill}$, Db denotes a distance from the object-side incidence surface $S_{ob}$ up to the object-side emergence surface $SB_{ill}$, and Dc denotes a distance from the object-side incidence surface $S_{ob}$ up to the object-side emergence surface $SC_{ill}$.

As mentioned above, in the endoscope of the present embodiment, it is possible to acquire an image in which the depth of field is widened. This is because of the fact that the objective unit 2 has the first optical path and the second optical path, and the optical-path length of first optical path and the optical-path length of the second optical path differ.

As the difference in the optical-path length of the first optical path and the optical-path length of the second optical path (hereinafter, referred to as 'optical-path length difference') is made larger, the depth of field widens. As the depth of field is widened, a position of a far point in the depth of field moves away from the objective unit. Moreover a position of a near point in the depth of field comes closer to the objective unit 2.

Figure 3:
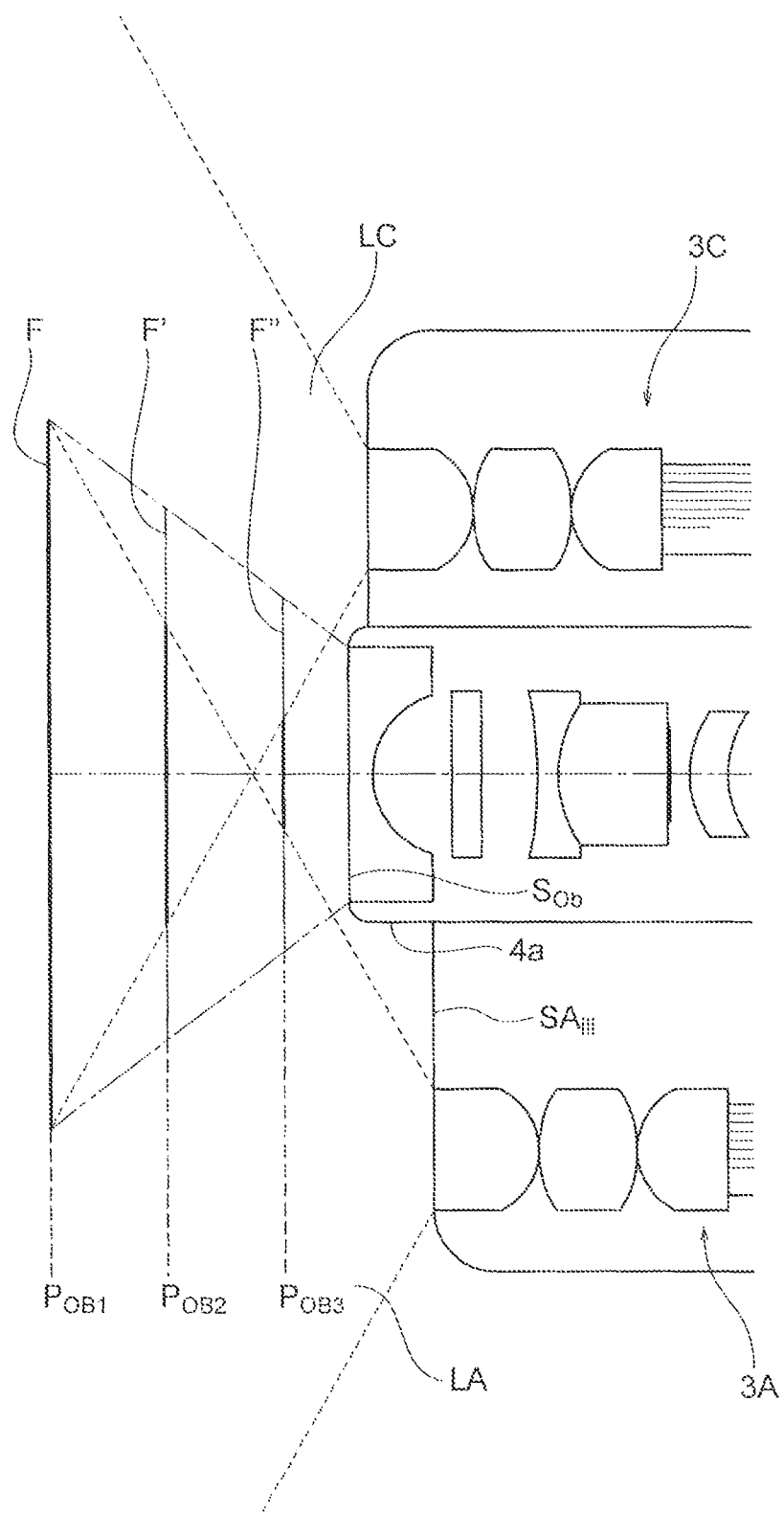
FIG. 3 is a diagram showing an appearance of an illumination unevenness.

An appearance of an illumination unevenness is shown in FIG. 3. In FIG. 3, a position $P_{OB1}$ at a near point before widening of the depth of field and a position $P_{OB2}$ at a near point after widening of the depth of field are shown. Moreover, a position $P_{OB3}$ is shown as reference. The position $P_{OB3}$ at the near point is located near the objective unit 2 than the position $P_{OB2}$ at the near point.

An illumination range of the illumination light LA irradiated from the illuminating optical system 3A changes according to a distance from the illuminating optical system up to an object. Similar is true for the illuminating optical system 3B and the illuminating optical system 3C.

In a case in which the position $P_{OB1}$ is the object position, at the position $P_{OB1}$, a part of the illumination light LA and a part of the illumination light LC overlap. A range in which the two illumination lights overlap is indicated by a thick line. The range in which the two illumination lights overlap substantially coincides with the field of view F. In this case, the illumination unevenness in the field of view F is less.

In a case in which, the position $P_{OB2}$ is the object position, even at the position $P_{OB2}$, a part of the illumination light LA and a part of the illumination light LC overlap. A range in which the two illumination lights overlap is indicated by a thick line. The range in which the two illumination lights overlap is restricted to a part of the field of view F.

In this case, there occurs a difference in brightness of the illumination light in the range in which the two illumination lights overlap and in a range in which the two illumination lights do not overlap. Consequently, the illumination unevenness is largely conspicuous for the illumination at the position $P_{OB2}$ as compared to the illumination unevenness for an illumination at the position $P_{OB1}$.

In a case in which the position $P_{OB3}$ is the object position, at the position $P_{OB3}$, the illumination light LA and the illumination light LB cease to overlap. A range in which the two illumination lights are not irradiated is indicated by a thick line. In this case, the observation is hindered due to a part of the field of view F not being illuminated.

As just described, as the depth of field widens, the illumination unevenness becomes conspicuous, particularly at a position of a near point.

The object-side incidence surface $S_{ob}$ is located nearest to the object. This gives rise to a level difference between the object-side incidence surface $S_{ob}$ and the object-side emergence surface $SA_{ill}$ for instance. The larger the level difference, a length of a side surface 4a of the level difference also becomes longer. Consequently, as the object-side emergence surface $SA_{ill}$ moves away from the object-side incidence surface $S_{ob}$, toward the image side, a part of the illumination light is shielded at the side surface 4a.

In this case, the illumination unevenness becomes conspicuous not only at the position of a near point but also at a position of a far point. Therefore, in an apparatus which enables to acquire an image in which the depth of field is widened, it becomes significant that the optical-path length difference and the depth amount have been set appropriately.

For such reason, the endoscope of the present embodiment satisfies conditional expression (1). Conditional expression (1) is a conditional expression about the minimum of the depth amount (hereinafter, referred to as 'minimum depth amount') and the optical-path length difference.

By satisfying conditional expression (1), it is possible to make appropriate a relationship of the optical-path length difference and the minimum depth amount. Consequently, even in a case of acquiring an image in which the depth of field is widened, it is possible to reduce the illumination unevenness adequately.

In a case in which a value falls below a lower limit value of conditional expression (1), the minimum depth amount becomes excessively small. Consequently, the illumination unevenness occurs remarkably.

In a case in which the minimum depth amount is zero, the position of the object-side emergence surface $SA_{ill}$ coincides with a position of the object-side incidence surface $S_{ob}$. For making such arrangement, for instance, the object-side emergence surface $SA_{ill}$ is to be moved toward the object side. However, when the object-side emergence surface $SA_{ill}$ is moved toward the object side, at the position $P_{OB1}$ and the position $P_{OB2}$, the range in which the two illumination lights overlap decreases. Moreover, at the position $P_{OB3}$, the range in which the two illumination lights are not irradiated increases.

In a case in which, the value exceeds an upper limit value of conditional expression (1), the minimum depth amount becomes excessively large. In this case, a part of the illumination light is shielded at the side surface 4a. Consequently, a part of the illumination light does not emerge from a front-end portion. As a result, the illumination unevenness occurs remarkably.

It is preferable that following conditional expression (1') be satisfied instead of conditional expression (1).

$$2.5 \leq D\mathrm{min}/\mathrm{OPLdiff} \leq 30 \qquad (1')$$

It is more preferable that following conditional expression (1") be satisfied instead of conditional expression (1).

$$2.8 \leq D\mathrm{min}/\mathrm{OPLdiff} \leq 10 \qquad (1")$$

In acquiring an image in which the depth of field is widened, an image sensor is used. It is preferable to capture two optical images by one image sensor. When such an arrangement is made, since only one image sensor serves the purpose, it is possible to reduce cost.

In the endoscope of the present embodiment, it is preferable that the objective optical system include a lens which moves in the optical axial direction, switching between a magnified observation and a normal observation can be carried out by moving the lens, and following conditional expressions (2) and (3) be satisfied:

$$0.1 < D\min^2/(OPL\text{diff} \times D\text{focus}) < 30 \quad (2)$$

$$1.01 < \omega(\text{wide})/\omega(\text{tele}) < 5.0 \quad (3)$$

where,

Dmin denotes the minimum of the depth amounts, and the depth amount is the distance in the optical axial direction from the object-side incidence surface up to the object-side emergence surface, OPLdiff denotes the difference in the optical-path length of the first optical path and the optical-path length of the second optical path, Dfocus denotes an amount of movement of the lens, ω(wide) denotes an angle of view of the objective optical system in a normal observation state, and ω(tele) denotes an angle of view of the objective optical system in a magnified observation state.

Figure 4A:
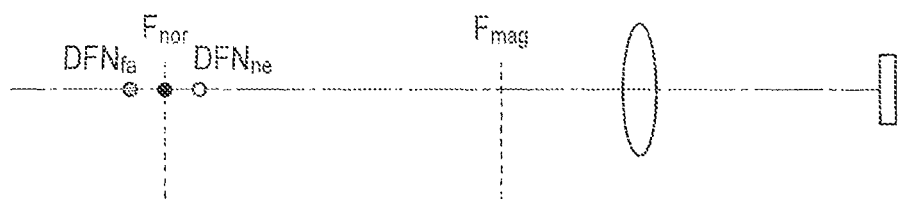
FIG. 4A, FIG. 4B, FIG. 4C, and FIG. 4D are diagrams showing an outline of a depth of field.
Figure 4B:
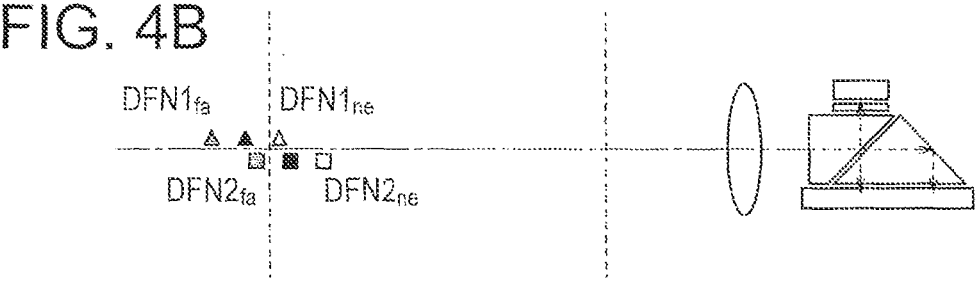
Figure 4C:
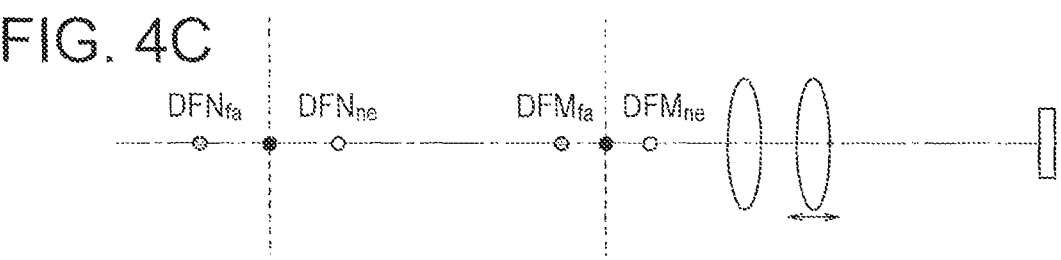
Figure 4D:
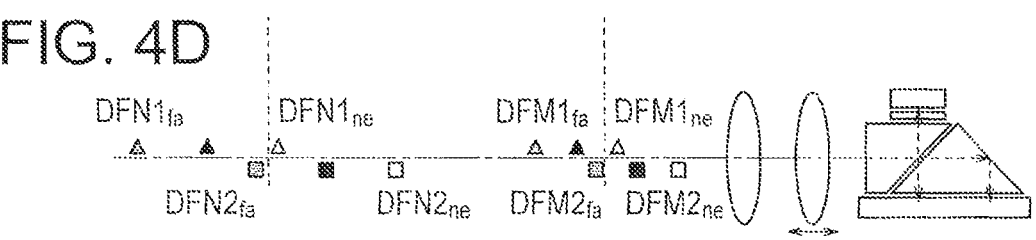

An outline of the depth of field is shown in FIG. 4A, FIG. 4B, FIG. 4C, and FIG. 4D. FIG. 4A shows a depth of field for a first optical system, FIG. 4B shows a depth of field for a second optical system, FIG. 4C shows a depth of field for a third optical system, and FIG. 4D shows a depth of field for a fourth optical system.

A position $F_{nor}$ is a focus position in the normal observation. A position $F_{mag}$ is a focus position in the magnified observation. A position of an object in the magnified observation is nearer from the optical system than an object position in the normal observation. In the magnified observation, it is possible to observe an object with a high magnification ratio as in a microscopic observation.

Difference in optical systems is as follows.

| Difference in optical systems is as follows. | | |
|---|---|---|
| | Movement of lens | Optical-path splitting member |
| First optical system | No | No |
| Second optical system | No | Yes |
| Third optical system | Yes | No |
| Fourth optical system | Yes | Yes |

In the first optical system, it is possible to carry out the normal observation. The first optical system does not include an optical-path splitting member. Therefore, it is not possible to acquire an image in which the depth of field is widened. The depth of field for the first optical system is a range from a position $DFN_{fa}$ up a position $DFN_{ne}$.

In the second optical system, it is possible to carry out the normal observation. The second optical system includes an optical-path splitting member. Therefore, it is possible to acquire an image in which the depth of field is widened.

A depth of field for a first optical path is a range from a position $DFN1_{fa}$ up to a position $DFN1_{ne}$. A depth of field for a second optical path is a range from a position $DFN2_{fa}$ up to a position $DFN2_{ne}$. Therefore, a depth of field for the second optical system is a range from the position $DFN1_{fa}$ up to the position $DFN2_{ne}$.

In the third optical system, it is possible to carry out the normal observation and the magnified observation. The third optical system does not include an optical-path splitting member. Therefore, in any of the normal observation and the magnified observation, it is not possible to acquire an image in which the depth of field is widened.

A depth of field in the normal observation is a range from a position $DFN_{fa}$ up to a position $DFN_{ne}$. A depth of field in the magnified observation is a range from a position $DFMf_{a}$ up to a position $DFM_{ne}$.

In the fourth optical system, it is possible to carry out the normal observation and the magnified observation. The fourth optical system includes an optical-path splitting member. Therefore, in any of the normal observation and the magnified observation, it is possible to acquire an image in which the depth of field is widened.

In the normal observation, a depth of field for the first optical path is the range from the position $DFN1_{fa}$ up to the position $DFN1_{ne}$. A depth of field for the second optical path is the range from the position $DFN2_{fa}$ up to the position $DFN2_{ne}$. Accordingly, a depth of field in the normal observation is a range from the position $DFN1_{fa}$ up to the position $DFN2_{ne}$.

In the magnified observation, a depth of field for the first optical path is a range from the position $DFM1_{fa}$ up to the position $DFM1_{ne}$. The depth of field for the second optical path is a range from the position $DFM2_{fa}$ up to the position $DFM2_{ne}$. Accordingly, the depth of field in the magnified observation is a range from the position $DFM1_{fa}$ up to the position $DFM2_{ne}$.

A position $DFM_{ne}$ for the third optical system and a position $DFM2_{ne}$ for the fourth optical system are positions of near points in the depth of field. As it is evident upon comparing FIG. 4C and FIG. 4D, the position $DFM2_{ne}$ is located nearer to the optical system than the position $DFM_{ne}$.

As mentioned above, with the position of the near point coming closer to the front-end portion, the illumination unevenness becomes conspicuous. Therefore, in the optical system which enables the normal observation and the magnified observation, it becomes significant that the amount of movement of the lens has been set appropriately, in addition to the optical-path length difference and the depth amount being set appropriately.

Conditional expression (2) is a conditional expression related to the minimum depth amount, the optical-path length difference, and the amount of movement of the lens. By satisfying conditional expression (2), it is possible to make appropriate the relationship of the minimum depth amount, the optical-path length difference, and the amount of movement of the lens. Consequently, it is possible to reduce the illumination unevenness adequately even in a case of acquiring an image in which the depth of field is widened, in the magnified observation.

In the magnified observation, the position of the near point becomes closer to the front-end portion. By satisfying conditional expression (2), it is possible to have an illumination with less unevenness even at a position of a near point in the magnified observation.

In a case in which a value falls below a lower limit value of conditional expression (2), the minimum depth amount becomes excessively small. Consequently, the illumination unevenness occurs remarkably. In a case in which the value exceeds an upper limit value of conditional expression (2), the minimum depth amount becomes excessively large. Consequently, the illumination unevenness occurs remarkably. The cause for the occurrence of the illumination unevenness is as described in the technical significance of conditional expression (1).

Conditional expression (3) is a conditional expression which regulates a change in the angle of view in the magnified observation and the normal observation. By satisfying conditional expression (3), an appropriate change in the angle of view occurs. It is possible to reduce the illumination unevenness at the time of magnified observation, while causing an area of a field of view in the magnified observation to differ from an area of a field of view in the normal observation.

A characteristic of the magnified observation is that a more detailed observation as compared to the normal observation is possible. In a case in which a value falls below a lower limit value of conditional expression (3), almost no variation in the angle of view occurs even when the lens is moved. Consequently, it is not possible to make full use of the characteristic of the magnified observation.

In a case in which the value exceeds a lower limit value of conditional expression (3), the variation in the angle of view due to the movement of the lens becomes excessively large. In this case, the angle of view in the magnified observation becomes remarkably small. For carrying out the magnified observation, position adjustment of a part to be observed and a center of the field of view, is carried out in the normal observation. When the angle of view in the magnified observation is remarkably small, it takes time for position adjustment in the normal observation. Consequently, a smooth observation becomes difficult.

It is preferable that following conditional expression (2') be satisfied instead of conditional expression (2).

$$0.5 < D\text{min}^2/(OPL\text{diff} \times D\text{focus}) < 10 \tag{2'}$$

It is more preferable that following conditional expression (2") be satisfied instead of conditional expression (2).

$$1.0 < D\text{min}^2/(OPL\text{diff} \times D\text{focus}) < 6.5 \tag{2"}$$

It is preferable that following conditional expression (3') be satisfied instead of conditional expression (3).

$$1.02 < \omega(\text{wide})/\omega(\text{tele}) < 2.0 \tag{3'}$$

It is more preferable that following conditional expression (3") be satisfied instead of conditional expression (3).

$$1.03 < \omega(\text{wide})/\omega(\text{tele}) < 1.1 \tag{3"}$$

In the endoscope of the present embodiment, it is preferable that following conditional expression (4) be satisfied:

$$0.2 < D\text{ave}^2/(OPL\text{diff} \times D\text{focus}) < 50 \tag{4}$$

where,

Dave denotes an average of the depth amounts, and the depth amount is the distance in the optical axial direction from the object-side incidence surface up to the object-side emergence surface, OPLdiff denotes the difference in the optical-path length of the first optical path and the optical-path length of the second optical path, and Dfocus denotes an amount of movement of the lens.

Conditional expression (4) is a conditional expression related to the average of the depth amounts, the optical-path length difference, and the amount of movement of the lens. By satisfying conditional expression (4), it is possible to make appropriate the relationship of the average of the depth amount, the optical-path length difference, and the amount of movement of the lens. Consequently, it is possible to reduce the illumination unevenness adequately even in a case of acquiring an image in which the depth of field is widened in the magnified observation.

In a case in which a value falls below a lower limit value of conditional expression (4), the average of the depth amount becomes excessively small. Consequently, the illumination unevenness occurs remarkably. In a case in which the value exceeds an upper limit value of conditional expression (4), the average of the depth amount becomes excessively large. Consequently, the illumination unevenness occurs remarkably. The cause for the occurrence of the illumination unevenness is as described in the technical significance of conditional expression (1).

It is preferable that following conditional expression (4') be satisfied instead of conditional expression (4).

$$0.6 < D\text{ave}^2/(OPL\text{diff} \times D\text{focus}) < 20 \tag{4'}$$

It is more preferable that following conditional expression (4") be satisfied instead of conditional expression (4).

$$1.5 < D\text{ave}^2/(OPL\text{diff} \times D\text{focus}) < 7.0 \tag{4"}$$

In the endoscope of the present embodiment, it is preferable that following conditional expression (5) be satisfied:

$$0.3 < D\text{max}^2/(OPL\text{diff} \times D\text{focus}) < 80 \tag{5}$$

where,

Dmax denotes a maximum of the depth amounts, and the depth amount is the distance in the optical axial direction from the object-side incidence surface up to the object-side emergence surface, OPLdiff denotes the difference in the optical-path length of the first optical path and the optical-path length of the second optical path, and Dfocus denotes the amount of movement of the lens.

Conditional expression (5) is a conditional expression related to the maximum of the depth amounts (hereinafter, referred to as 'maximum depth amount'), the optical-path length difference, and the amount of movement of the lens. By satisfying conditional expression (5), it is possible to make appropriate a relationship of the maximum depth amount, the optical-path length difference, and the amount of movement of the lens. Consequently, it is possible to reduce the illumination unevenness adequately even in a case of acquiring an image in which the depth of field is widened in the magnified observation.

In a case in which a value falls below a lower limit value of conditional expression (5), the maximum depth amount becomes excessively small. Consequently, the illumination unevenness occurs remarkably. In a case in which the value exceeds an upper limit value of conditional expression (5), the maximum depth amount becomes excessively large. Consequently, the illumination unevenness occurs remarkably. The cause for the occurrence of the illumination unevenness is as described in the technical significance of conditional expression (1).

It is preferable that following conditional expression (5') be satisfied instead of conditional expression (5).

$$1.0 < D\text{max}^2/(OPL\text{diff} \times D\text{focus}) < 60 \tag{5'}$$

It is more preferable that following conditional expression (5") be satisfied instead of conditional expression (5).

$$4.0 < D\text{max}^2/(OPL\text{diff} \times D\text{focus}) < 40 \tag{5"}$$

In the endoscope of the present embodiment, it is preferable that an amount of illumination light and an angle of emergence of the illumination light be substantially same for all of the plurality of illuminating optical systems.

The endoscope of the present embodiment includes the plurality of illuminating optical systems. In the endoscope of the present embodiment, the amount of light and the angle of emergence of light from each illuminating optical system are made substantially same. By making such arrangement, it is possible to suppress a manufacturing cost.

It is preferable that the endoscope of the present embodiment include three illuminating optical systems.

When the number of illuminating optical systems is made three, it is possible to suppress the illumination unevenness while suppressing a diameter of the front-end portion from becoming large.

Examples of the objective optical system to be used in the endoscope of the present embodiment will be described below in detail by referring to the accompanying diagrams. However, the present disclosure is not restricted to the examples described below.

Figure 5A:
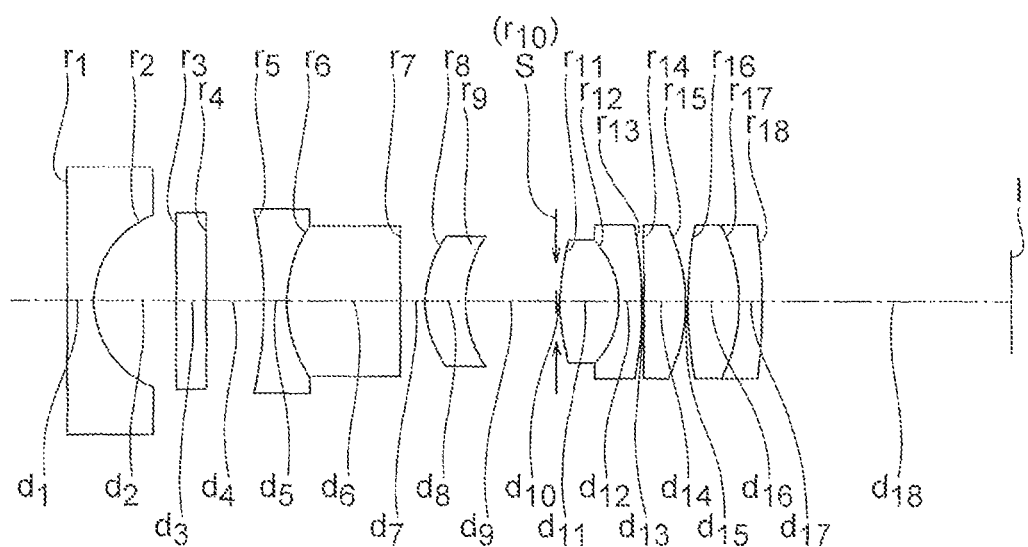
FIG. 5A and FIG. 5B are cross-sectional views of an objective optical system of an example 1.
Figure 5B:
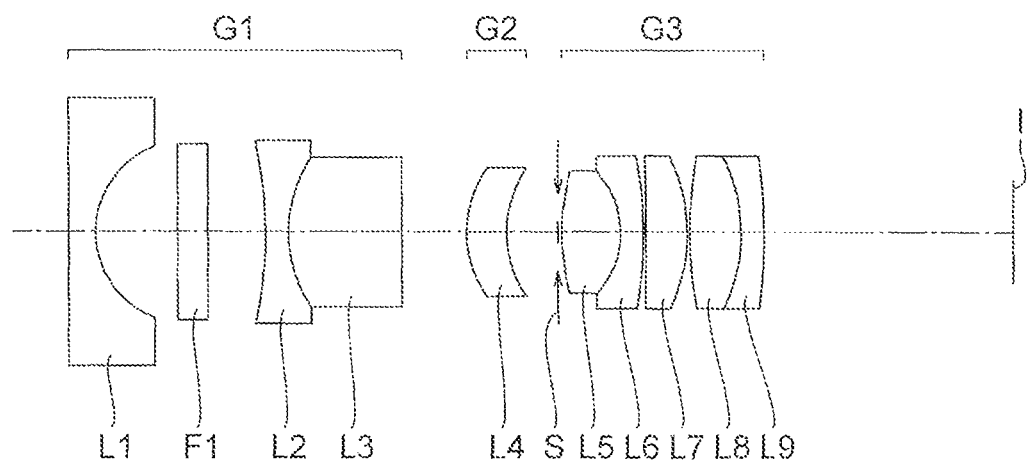
Figure 7A:
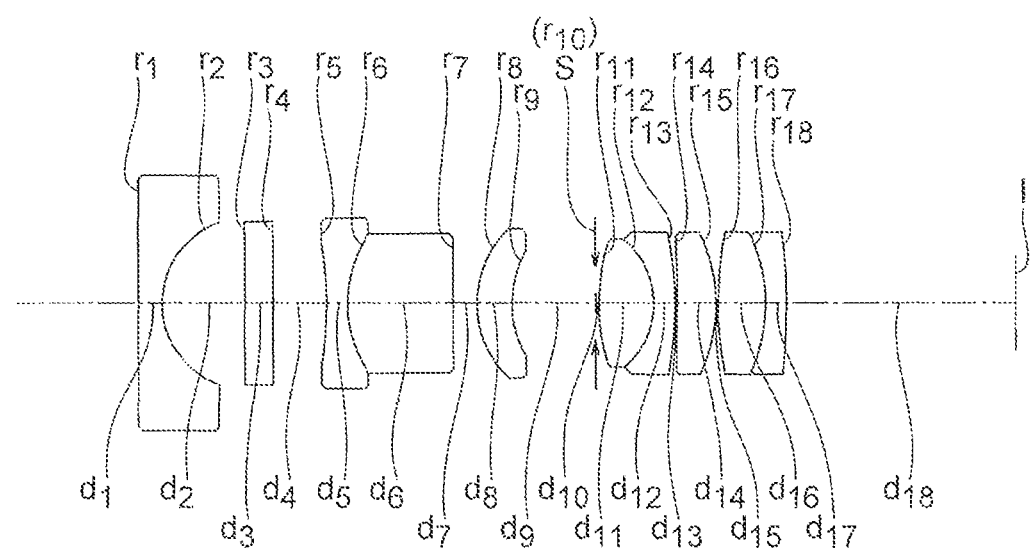
FIG. 7A and FIG. 7B are cross-sectional views of an objective optical system of an example 2.
Figure 7B:
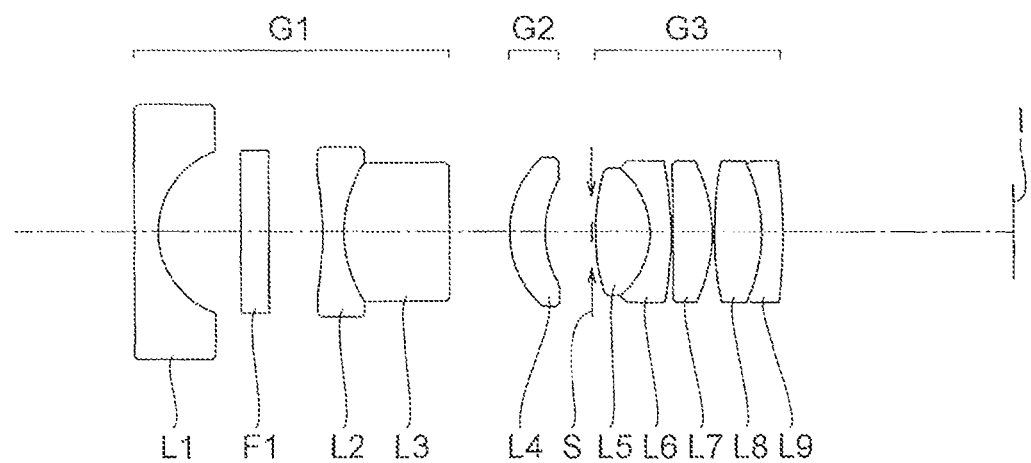
Figure 9A:
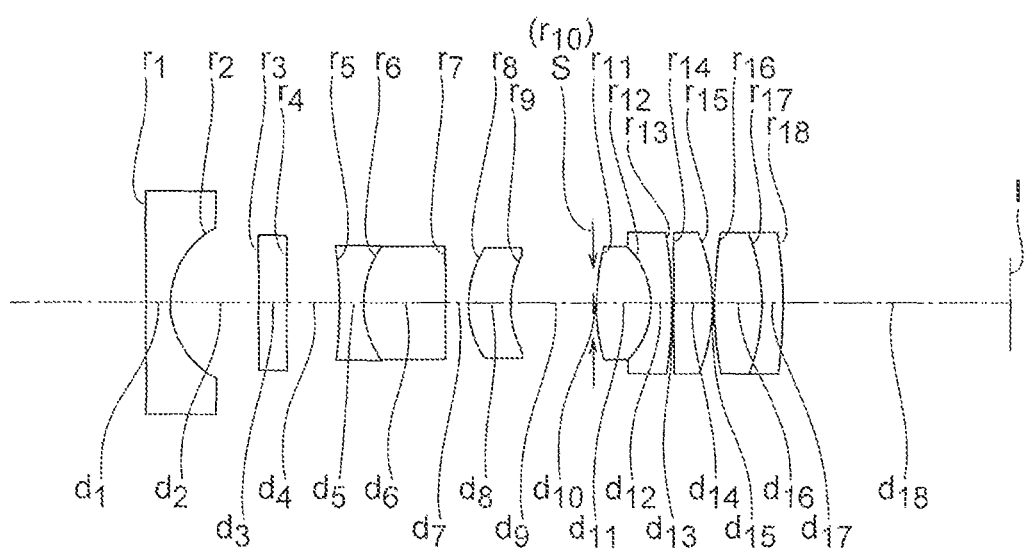
FIG. 9A and FIG. 9B are cross-sectional views of an objective optical system of an example 3.
Figure 9B:
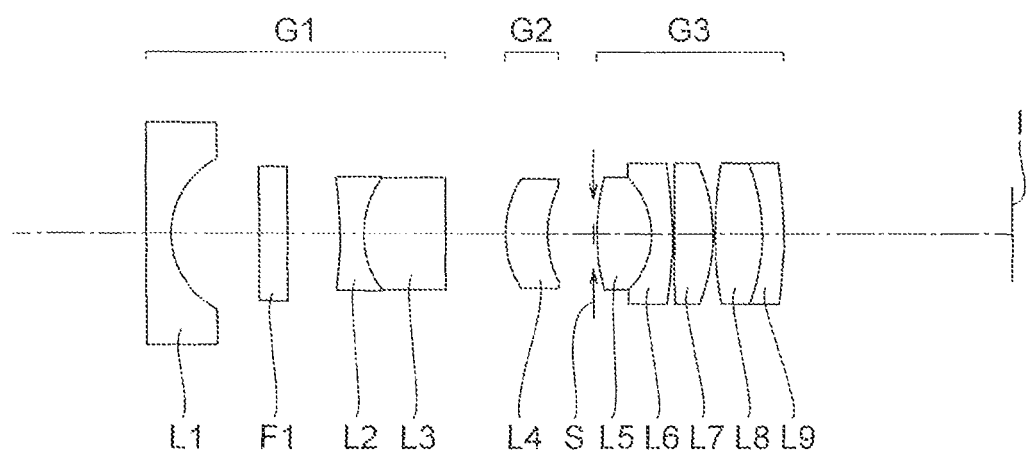

Lens cross-sectional views of each example will be described below. FIG. 5A, FIG. 7A, and FIG. 9A are lens cross-sectional views in a normal observation state, and FIG. 5B, FIG. 7B, and FIG. 9B are lens cross-sectional views in a magnified observation state.

A first lens group is denotes by G1, a second lens group is denoted by G2, a third lens group is denoted by G3, and aperture stop is denoted by S, and an image plane (image pickup surface) is denoted by I. A plane parallel plate is denoted by F1.

The plane parallel plate F is a filter for cutting off light of specific wavelengths such as laser light of YAG (yttrium aluminum garnet) laser (light of wavelength 1060 nm), laser light of semiconductor laser (light of wavelength 810 nm), or light of wavelength in a near-infrared region.

Description of aberration diagrams for each example is as follows.

Aberration diagrams in the normal observation state are as follow.

Figures 8A, 8B, 8C, 8D:
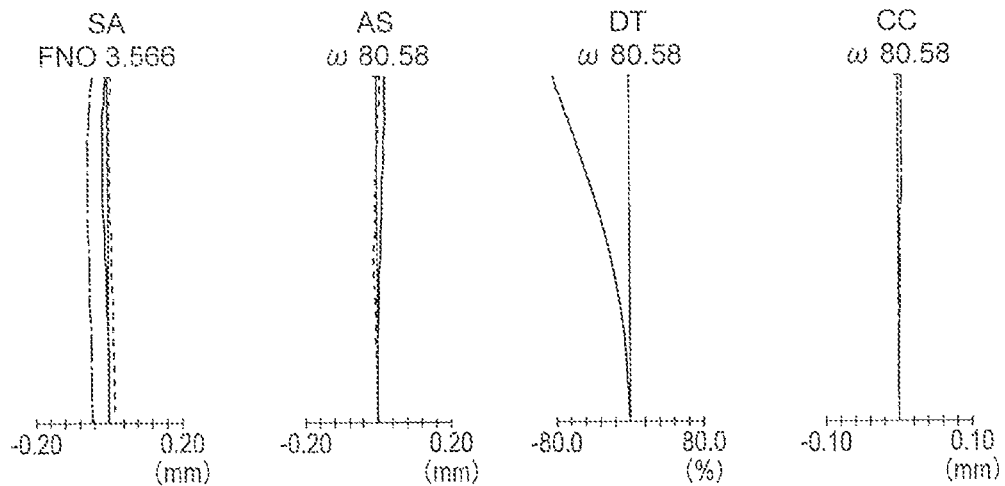
FIG. 8A, FIG. 8B, FIG. 8C, FIG. 8D, FIG. 8E, FIG. 8F, FIG. 8G, and FIG. 8H are aberration diagrams of the objective optical system of the example 2.
Figures 10A, 10B, 10C, 10D:
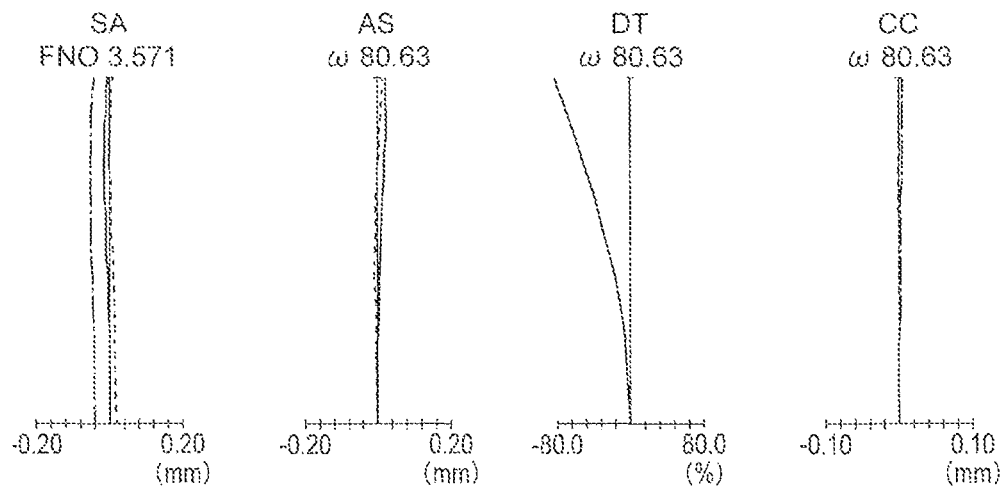
FIG. 10A, FIG. 10B, FIG. 10C, FIG. 10D, FIG. 10E, FIG. 10F, FIG. 10G, and FIG. 10H are aberration diagrams of the objective optical system of the example 3.

FIG. 6A, FIG. 8A, and FIG. 10A show a spherical aberration (SA). FIG. 6B, FIG. 8B, and FIG. 10B show an astigmatism (AS). FIG. 6C, FIG. 8C, and FIG. 10C show a distortion (DT). FIG. 6D, FIG. 8D, and FIG. 10D show a chromatic aberration of magnification (CC).

Aberration diagrams in the magnified observation state are as follow.

Figures 8E, 8F, 8G, 8H:
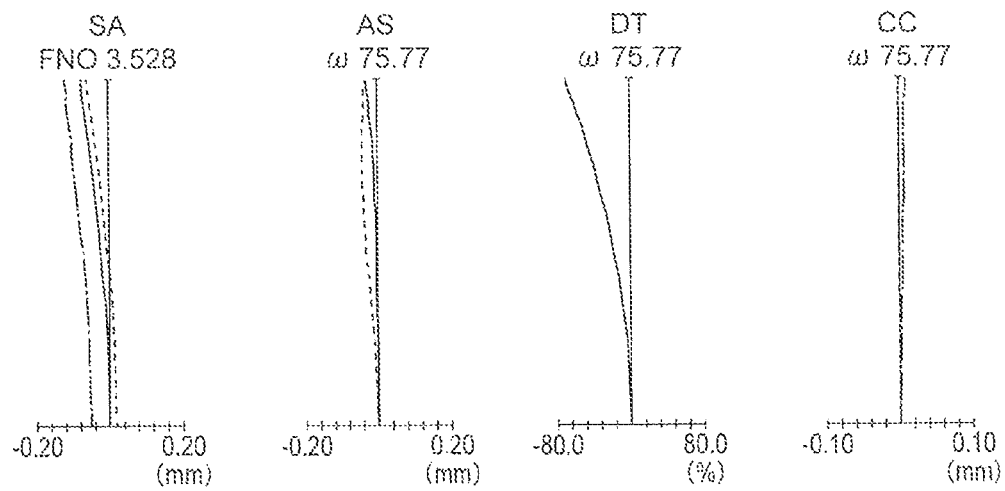
Figures 10E, 10F, 10G, 10H:
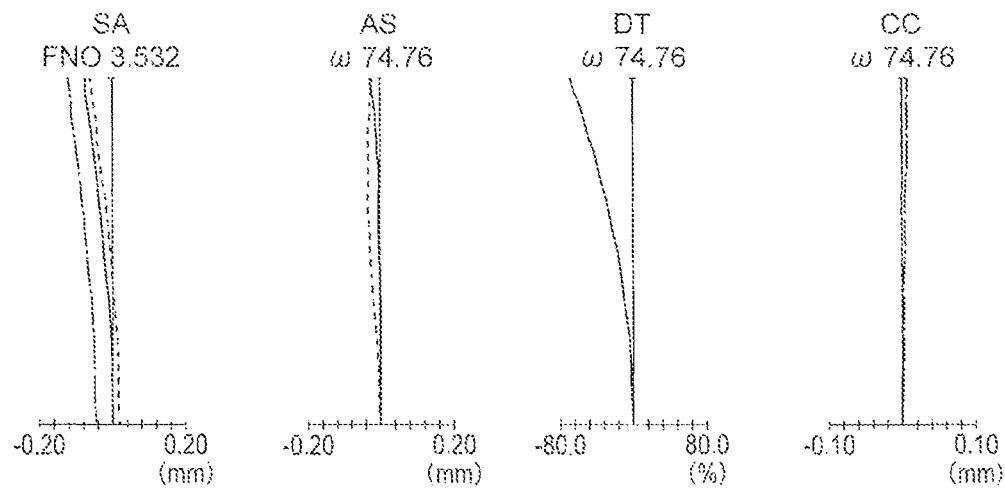

FIG. 6E, FIG. 8E, and FIG. 10E show a spherical aberration (SA). FIG. 6F, FIG. 8F, and FIG. 10F show an astigmatism (AS). FIG. 6G, FIG. 8G, and FIG. 10G show a distortion (DT). FIG. 6H, FIG. 8H, and FIG. 10H show a chromatic aberration of magnification (CC).

In each aberration diagram, a horizontal axis indicates an aberration amount. For the spherical aberration, the astigmatism, and the chromatic aberration, the unit of aberration amount is mm. For the distortion, the unit of aberration amount is %. Moreover, FNO denotes an F-number, co denotes a half angle of view and the unit thereof is ° (degree). Furthermore, the unit of a wavelength of an aberration curve is nm.

Example 1

An objective optical system of an example 1 includes in order from an object side, a first lens group G1 having a negative refractive power, a second lens group G2 having a positive refractive power, and a third lens group G3 having a positive refractive power.

The first lens group G1 includes a planoconcave negative lens L1, a biconcave negative lens L2, and a planoconvex positive lens L3. Here, the biconcave negative lens L2 and the planoconvex positive lens L3 are cemented.

The second lens group G2 includes a positive meniscus lens L4 having a convex surface directed toward the object side.

The third lens group G3 includes a biconvex positive lens L5, a negative meniscus lens L6 having a convex surface directed toward an image side, a positive meniscus lens L7 having a convex surface directed toward the image side, a biconvex positive lens L8, and a negative meniscus lens L9 having a convex surface directed toward the image side. Here, the biconvex positive lens L5 and the negative meniscus lens L6 are cemented. The biconvex positive lens L8 and the negative meniscus lens L9 are cemented.

At the time of switching from a normal observation to a magnified observation, the second lens group G2 is moved toward the image side.

A plane parallel plate F1 (optical filter) is disposed between the planoconcave negative lens L1 and the biconcave negative lens L2. An aperture stop S is disposed between the second lens group G2 and the third lens group G3.

Example 2

An objective optical system of an example 2 includes in order from an object side, a first lens group G1 having a negative refractive power, a second lens group G2 having a positive refractive power, and a third lens group G3 having a positive refractive power.

The first lens group G1 includes a planoconcave negative lens L1, a biconcave negative lens L2, and a planoconvex positive lens L3. Here, the biconcave negative lens L2 and the planoconvex positive lens L3 are cemented.

The second lens group G2 includes a positive meniscus lens L4 having a convex surface directed toward the object side.

The third lens group G3 includes a biconvex positive lens L5, a negative meniscus lens L6 having a convex surface directed toward an image side, a positive meniscus lens L7 having a convex surface directed toward the image side, a biconvex positive lens L8, and a negative meniscus lens L9 having a convex surface directed toward the image side. Here, the biconvex positive lens L5 and the negative meniscus lens L6 are cemented. The biconvex positive lens L8 and the negative meniscus lens L9 are cemented.

At the time of switching from a normal observation to a magnified observation, the second lens group G2 is moved toward the image side.

A plane parallel plate F1 (optical filter) is disposed between the planoconcave negative lens L1 and the biconcave negative lens L2. An aperture stop S is disposed between the second lens group G2 and the third lens group G3.

Example 3

An objective optical system of an example 3 includes in order from an object side, a first lens group G1 having a negative refractive power, a second lens group G2 having a positive refractive power, and a third lens group G3 having a positive refractive power.

The first lens group G1 includes a planoconcave negative lens L1, a biconcave negative lens L2, and a planoconvex positive lens L3. Here, the biconcave negative lens L2 and the planoconvex positive lens L3 are cemented.

The second lens group G2 includes a positive meniscus lens L4 having a convex surface directed toward the object side.

The third lens group G3 includes a biconvex positive lens L5, a negative meniscus lens L6 having a convex surface directed toward an image side, a biconvex positive lens L7, a biconvex positive lens L8, and a negative meniscus lens L9 having a convex surface directed toward the image side. Here, the biconvex positive lens L5 and the negative meniscus lens L6 are cemented. The biconvex positive lens L8 and the negative meniscus lens L9 are cemented.

At the time of switching from a normal observation to a magnified observation, the second lens group G2 is moved toward the image side.

A plane parallel plate F1 (optical filter) is disposed between the planoconcave negative lens L1 and the biconcave negative lens L2. An aperture stop S is disposed between the second lens group G2 and the third lens group G3.

Numerical data for each example is shown below. In surface data, r denotes a radius of curvature of each lens surface, d denotes a distance between two lenses, nd denotes a refractive index for a d-line of each lens, and vd denotes Abbe's number for each lens. A stop denotes an aperture stop.

In Various data, f denotes a focal length for the d-line, Fno denotes an F-number, ω denotes a half angle of view, fb denotes a back focus, and LTL denotes a total length. The total length is obtained by adding the back focus to a distance from a lens front-most surface up to a lens rear-most surface. The back focus is a distance from the lens rear-most surface up to a paraxial image plane, subjected to air conversion.

Example 1

Unit mm

| Surface data | | | | |
|---|---|---|---|---|
| Surface no. | r | d | nd | vd |
| 1 | ∞ | 0.52 | 1.88300 | 40.76 |
| 2 | 1.756 | 1.61 | | |
| 3 | ∞ | 0.59 | 1.52100 | 65.12 |
| 4 | ∞ | 1.12 | | |
| 5 | −7.847 | 0.44 | 1.88300 | 40.76 |
| 6 | 2.604 | 2.21 | 1.84666 | 23.78 |
| 7 | ∞ | d7 | | |
| 8 | 2.132 | 0.78 | 1.48749 | 70.23 |
| 9 | 2.217 | d9 | | |
| 10 (Stop) | ∞ | 0.07 | | |
| 11 | 4.230 | 1.15 | 1.67270 | 32.10 |
| 12 | −1.724 | 0.44 | 2.00330 | 28.27 |
| 13 | −7.952 | 0.04 | | |
| 14 | −70.606 | 0.81 | 1.69895 | 30.13 |
| 15 | −3.332 | 0.04 | | |
| 16 | 7.886 | 0.99 | 1.48749 | 70.23 |
| 17 | −3.344 | 0.44 | 1.95906 | 17.47 |
| 18 | −11.310 | fb | | |

Image pickup surface ∞

| Various data | | |
|---|---|---|
| | Normal observation state | Close observation state |
| f | 1.00 | 1.00 |
| FNO. | 3.57 | 3.53 |
| 2ω | 158.56 | 151.28 |
| fb (in air) | 4.78 | 4.70 |
| LTL (in air) | 18.30 | 18.22 |
| d7 | 0.48 | 1.25 |
| d9 | 1.75 | 0.99 |

| Unit focal length | | |
|---|---|---|
| f1 = −1.20 | f2 = 28.29 | f3 = 3.55 |

Example 2

Unit mm

| Surface data | | | | |
|---|---|---|---|---|
| Surface no. | r | d | nd | vd |
| 1 | ∞ | 0.52 | 1.88300 | 40.76 |
| 2 | 1.790 | 1.74 | | |
| 3 | ∞ | 0.59 | 1.52100 | 65.12 |
| 4 | ∞ | 1.12 | | |
| 5 | −7.773 | 0.44 | 1.88300 | 40.76 |
| 6 | 2.611 | 2.22 | 1.84666 | 23.78 |
| 7 | ∞ | d7 | | |
| 8 | 2.141 | 0.74 | 1.48749 | 70.23 |
| 9 | 2.227 | d9 | | |
| 10 (Stop) | ∞ | 0.07 | | |
| 11 | 4.313 | 1.16 | 1.67270 | 32.10 |
| 12 | −1.731 | 0.44 | 2.00330 | 28.27 |
| 13 | −7.595 | 0.04 | | |
| 14 | −55.368 | 0.82 | 1.69895 | 30.13 |
| 15 | −3.350 | 0.04 | | |
| 16 | 7.811 | 0.99 | 1.48749 | 70.23 |
| 17 | −3.406 | 0.44 | 1.95906 | 17.47 |
| 18 | −12.287 | fb | | |

Image pickup surface ∞

| Various data | | |
|---|---|---|
| | Normal observation state | Close observation state |
| f | 1.00 | 1.00 |
| FNO. | 3.57 | 3.53 |
| 2ω | 161.16 | 151.53 |
| fb (in air) | 4.80 | 4.72 |
| LTL (in air) | 18.46 | 18.39 |
| d7 | 0.48 | 1.26 |
| d9 | 1.76 | 0.99 |

| Unit focal length | | |
|---|---|---|
| f1 = 1.20 | f2 = 29.53 | f3 = 3.57 |

Example 3

Unit mm

| Surface data | | | | |
|---|---|---|---|---|
| Surface no. | r | d | nd | vd |
| 1 | ∞ | 0.52 | 1.88300 | 40.76 |
| 2 | 1.770 | 1.85 | | |
| 3 | ∞ | 0.59 | 1.52100 | 65.12 |
| 4 | ∞ | 1.12 | | |
| 5 | −8.674 | 0.52 | 1.88300 | 40.76 |
| 6 | 2.018 | 1.71 | 1.84666 | 23.78 |
| 7 | ∞ | d7 | | |
| 8 | 2.127 | 0.88 | 1.48749 | 70.23 |

-continued

Surface data

| Surface no. | r | d | nd | vd |
|---|---|---|---|---|
| 9 | 2.212 | d9 | | |
| 10 (Stop) | ∞ | 0.07 | | |
| 11 | 4.378 | 1.15 | 1.63854 | 55.38 |
| 12 | −1.665 | 0.44 | 1.88300 | 40.76 |
| 13 | −9.226 | 0.04 | | |
| 14 | 197.416 | 0.81 | 1.69895 | 30.13 |
| 15 | −3.827 | 0.04 | | |
| 16 | 8.514 | 0.99 | 1.48749 | 70.23 |
| 17 | −4.078 | 0.44 | 1.95906 | 17.47 |
| 18 | −10.722 | fb | | |

Image pickup surface ∞

Various data

| | Normal observation state | Close observation state |
|---|---|---|
| f | 1.00 | 1.00 |
| FNO. | 3.57 | 3.53 |
| 2ω | 161.27 | 149.52 |
| fb (in air) | 4.77 | 4.69 |
| LTL (in air) | 18.18 | 18.10 |
| d7 | 0.48 | 1.25 |
| d9 | 1.75 | 0.99 |

Unit focal length

| f1 = −1.21 | f2 = 25.60 | f3 = 3.53 |
|---|---|---|

Values of conditional expressions in each example are shown below.

| Conditional expression | Example 1 | Example 2 | Example 3 |
|---|---|---|---|
| (1) | 2.800 | 10.000 | 3.333 |
| (2) | 1.021 | 6.486 | 4.352 |
| (3) | 1.048 | 1.064 | 1.079 |
| (4) | 3.255 | 12.712 | 5.266 |
| (5) | 6.750 | 37.359 | 7.355 |

Values of parameters are shown below.

| | Example 1 | Example 2 | Example 3 |
|---|---|---|---|
| Dmin | 0.28 | 0.5 | 1 |
| OPLdiff | 0.1 | 0.05 | 0.3 |
| Dfocus | 0.768 | 0.7709 | 0.766 |
| Dave | 0.5 | 0.7 | 1.1 |
| Dmax | 0.72 | 1.2 | 1.3 |
| ω (wide) | 79.278 | 80.582 | 80.634 |
| ω (tele) | 75.642 | 75.766 | 74.762 |

Various embodiments of the present disclosure have been described heretofore. However, the present disclosure is not restricted only to the embodiments described heretofore, and embodiments in which arrangements of the embodiments described heretofore are combined appropriately without departing from the scope of the disclosure are also within the scope of the present disclosure.

According to the present disclosure, it is possible to provide an endoscope which enables an illumination with a small unevenness and to acquire an image in which the depth of field is widened.

The present disclosure is useful for an endoscope which enables an illumination with a small unevenness, and to acquire an image in which the depth of field is widened.

What is claimed is:

1. An endoscope comprising:
a plurality of illuminating optical systems;
an objective optical system, and
an optical-path splitting member, wherein
the optical-path splitting member has an optical element which forms a first optical path and a second optical path,
an optical-path length of the first optical path differs from an optical-path length of the second optical path,
illumination light is irradiated to an object from the plurality of illuminating optical systems,
the objective optical system has an object-side incidence surface which is located nearest to the object,
each of the plurality of illuminating optical systems has an object-side emergence surface which is located nearest to the object,
each of the object-side emergence surfaces is located on an image side of the object-side incidence surface, and
following conditional expression (1) is satisfied:

$$2.0 < D\text{min}/\text{OPLdiff} < 50 \tag{1}$$

where,
Dmin denotes a minimum of depth amounts, and the depth amount is a distance in an optical axial direction from the object-side incidence surface up to the object-side emergence surface, and
OPLdiff denotes a difference in the optical-path length of the first optical path and the optical-path length of the second optical path.

2. The endoscope according to claim 1, wherein
the objective optical system includes a lens which moves in the optical axial direction,
switching between a magnified observation and a normal observation can be carried out by moving the lens, and
following conditional expressions (2) and (3) are satisfied:

$$0.1 < D\text{min}^2/(\text{OPLdiff} \times D\text{focus}) < 30 \tag{2}$$

$$1.01 < \omega(\text{wide})/\omega(\text{tele}) < 5.0 \tag{3}$$

where,
Dfocus denotes an amount of movement of the lens,
ω(wide) denotes an angle of view of the objective optical system in a normal observation state, and
ω(tele) denotes an angle of view of the objective optical system in a magnified observation state.

3. The endoscope according to claim 1, wherein following conditional expression (4) is satisfied:

$$0.2 < D\text{ave}^2/(\text{OPLdiff} \times D\text{focus}) < 50 \tag{4}$$

where,
Dave denotes an average of the depth amounts, and the depth amount is the distance in the optical axial direction from the object-side incidence surface up to the object-side emergence surface, and
Dfocus denotes an amount of movement of the lens.

4. The endoscope according to claim 1, wherein following conditional expression (5) is satisfied:

$$0.3 < D\text{max}^2/(\text{OPLdiff} \times D\text{focus}) < 80 \tag{5}$$

where,
Dmax denotes a maximum of the depth amounts, and the depth amount is the distance in the optical axial direction from the object-side incidence surface up to the object-side emergence surface, and
Dfocus denotes an amount of movement of the lens.

5. The endoscope according to claim 1, wherein an amount of illumination light and an angle of emergence of the illumination light are substantially same for all of the plurality of illuminating optical systems.

6. The endoscope according to claim 1, wherein the endoscope includes three illuminating optical systems.

* * * * *